(12) United States Patent
Candreva

(10) Patent No.: US 12,403,293 B2
(45) Date of Patent: Sep. 2, 2025

(54) MEDICAL DEVICE FOR APPLYING SEMI-PERMANENT TATTOO INK

(71) Applicant: Jason Candreva, Malverne, NY (US)

(72) Inventor: Jason Candreva, Malverne, NY (US)

(73) Assignee: Jason Candreva, Malverne, NY (US)

( * ) Notice: Subject to any disclaimer, the term of this patent is extended or adjusted under 35 U.S.C. 154(b) by 794 days.

(21) Appl. No.: 17/454,173

(22) Filed: Nov. 9, 2021

(65) Prior Publication Data

US 2022/0143379 A1 May 12, 2022

Related U.S. Application Data

(60) Provisional application No. 63/111,758, filed on Nov. 10, 2020.

(51) Int. Cl.
*A61M 37/00* (2006.01)
*A61K 8/11* (2006.01)

(52) U.S. Cl.
CPC .......... *A61M 37/0084* (2013.01); *A61K 8/11* (2013.01); *A61K 2800/43* (2013.01); *A61K 2800/654* (2013.01); *A61M 2202/0468* (2013.01); *A61M 2205/051* (2013.01)

(58) Field of Classification Search
CPC .......... A61K 8/11; A61K 8/8158; A61K 8/85; A61K 8/86; A61K 8/90; A61K 2800/654; A61K 2800/412; A61K 2800/54; A61K 2800/43; A61M 35/003; A61M 37/00; A61M 37/0015; A61M 37/0084; A61M 37/0076; A61M 2202/0468; A61M 2205/051; A61M 2205/071; A61M 2205/123; A61Q 1/025; A61B 2090/395; A61B 90/39; A61B 90/92
See application file for complete search history.

(56) References Cited

U.S. PATENT DOCUMENTS 6,013,122 A * 1/2000 Klitzman ............... C09D 11/00
106/31.03
6,436,105 B1 * 8/2002 Passmore ............... A61B 90/39
606/116

FOREIGN PATENT DOCUMENTS

DE 29916971 * 1/2000
WO WO-2020033903 A1 * 2/2020 ............... A61K 8/11

* cited by examiner

*Primary Examiner* — Robert J Scruggs
(74) *Attorney, Agent, or Firm* — Darren Haber

(57) ABSTRACT

The disclosure relates to a medical device for applying a semi-permanent tattoo ink to mark patients for medical procedures, including but not limited to radiation therapy in the treatment of various types of cancer. The tattoo ink is removable or disappears over a period of time following intradermal application.

8 Claims, 1 Drawing Sheet

MEDICAL DEVICE FOR APPLYING SEMI-PERMANENT TATTOO INK

This application claims the benefit of U.S. Provisional Application No. 63/111,758, filed Nov. 10, 2020, the contents of which is hereby incorporated by reference.

Throughout this application, various publications are referenced, including referenced in parenthesis. The disclosures of all publications mentioned in this application in their entireties are hereby incorporated by reference into this application in order to provide additional description of the art to which this invention pertains and of the features in the art which can be employed with this invention.

BACKGROUND OF THE INVENTION

Cancer is among the leading causes of death worldwide. In 2018 alone there were 18.1 million new cases of cancer and 9.5 million cancer-related deaths worldwide. Radiation therapy is a type of cancer treatment that uses beams of intense energy to kill cancer cells. Radiation therapy is commonly applied to cancerous tumors because of its ability to target cancerous cells while sparing healthy tissues and organs. Radiation therapy is used to treat patients palliatively, curatively, and prophylactically, as well as pre-operatively to shrink tumors and post-operatively on the tumor bed. The impact of radiation therapy varies between different types and stages of cancer, with success rates of 90% or higher for patients in early stages of disease.

Each radiation therapy treatment typically takes about 20 minutes, however treatment must often be delivered daily for at least four weeks and often may last months. Preparing a patient to receive radiation therapy over this period of time typically requires marking the location of treatment, alignment marks, and triangulation and biangulation marks. These marks play an important role in positioning of the patient receiving radiation treatment, achieving reproducible set up, and accuracy of the treatment delivery, which must be precise on the order of <1 mm. The field center, field edge, and/or other reference points are all marked. Moreover, treatment frequently requires the marking of multiple treatment sites on the same patient if multiple or repeat treatments are required.

Non-invasive markings, such as traditional ink markers or pens, are inadequate for marking patients for radiation therapy due to their temporary nature, lasting only about 2 to 48 hours. Use of permanent tattoos for marking radiation fields provides the advantages of being easy to set up, quick to apply, and beneficial to the reproducibility of the delivery of radiation throughout the course of treatment. However, the use of permanent tattoo ink in radiation therapy permanently "scars" patients receiving treatment with undesirable and widespread markings. Moreover, patients suffering from cancer with religious beliefs that conflict with the use of permanent tattoo ink may reject treatment. Parents too, may not wish to have permanent tattoo ink and painful tattoo needles applied to their young children. As a result, many patients who would otherwise receive this cancer-altering treatment continue to suffer from cancer and die.

SUMMARY OF THE INVENTION

This invention provides a sterile, single-use tattoo device comprising:
a. a hypodermic safety needle, and
b. an ampoule containing a semi-permanent, disappearing tattoo ink.

This invention also provides a method for marking a patient for radiation therapy comprising a step of tattooing the patient with a semi-permanent, disappearing tattoo ink.

DETAILED DESCRIPTION OF THE INVENTION

Figure 1:
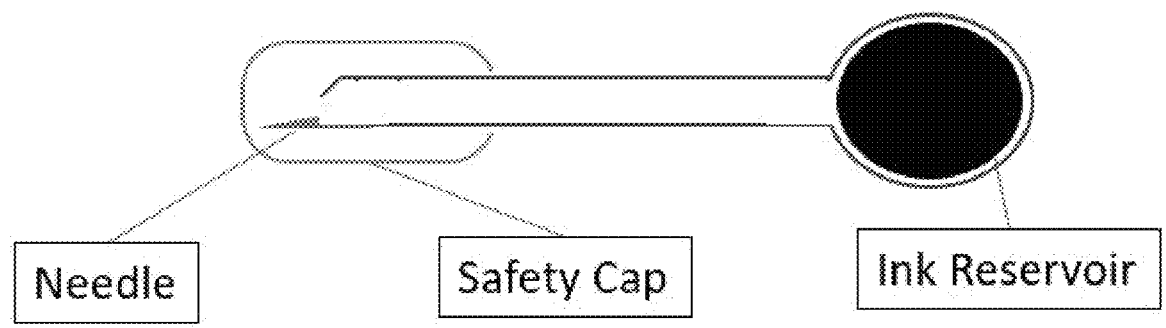
FIG. 1 shows a schematic representation of a semi-permanent ink tattoo applicator with integrated safety needle and ampoule (ink reservoir).
Figure 2:
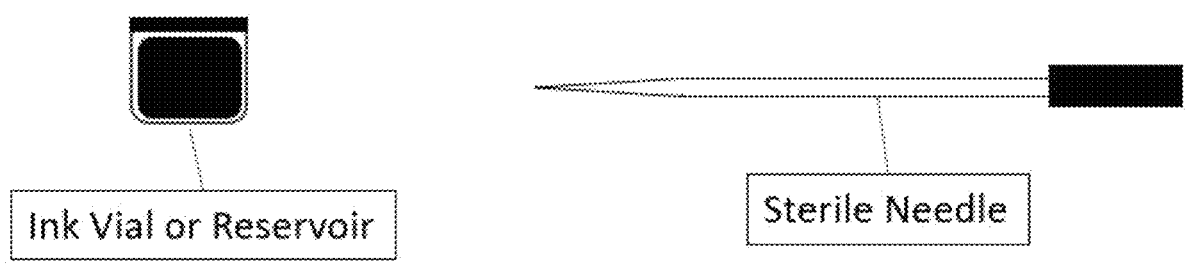
FIG. 2 shows a schematic representation of a semi-permanent ink tattoo applicator in which the needle and ink reservoir are separated.

This invention provides a sterile, single-use tattoo device comprising:
a. a hypodermic safety needle, and
b. an ampoule containing a semi-permanent, disappearing tattoo ink.

In embodiments, the semi-permanent, disappearing tattoo ink only remains visible to the naked eye for between 4 weeks and 18 months after it is tattooed on a patient's skin.

In embodiments, the semi-permanent, disappearing tattoo ink remains visible to the naked eye for less than one year.

In embodiments, the semi-permanent, disappearing tattoo ink is removed by the patient's immune system after it is tattooed on a patient's skin.

In embodiments, the patient's immune system does not begin removing the semi-permanent, disappearing tattoo ink for at least 2 weeks, preferably at least 4 weeks. In embodiments, the patient's immune system begins removing the semi-permanent, disappearing tattoo ink between 2 and 6 weeks after it is tattooed on a patient's skin. In embodiments, the patient's immune system begins removing the semi-permanent, disappearing tattoo ink between 2 and 4 weeks after it is tattooed on a patient's skin.

In embodiments, the ampoule is made of plastic and contains a breakable membrane which allows ink to flow at the time of tattoo application.

In embodiments, the semi-permanent, disappearing tattoo ink comprises:
a. particles, wherein the particles comprise:
  i. a shell comprising bioabsorbable and biodegradable polymer; and
  ii. a core comprising bioabsorbable and biodegradable polymers or a hydrogel matrix and a coloring agent having a molecular weight between 5 and $10 \times 10^6$ Daltons, wherein said coloring agent is intercalated, non-covalently, or covalently bound with the polymer or hydrogel matrix, and wherein the bioabsorbable and biodegradable polymer comprises a homopolymer, a copolymer, a diblock or triblock copolymer chosen from one or a combination of: polycaprolectone (PCL), poly L-lactic acid (PLLA), poly(lactic-co-glycolic acid) (PLGA), polyethylene glycol (PEG), polyethylene glycol-diacrylate (PEGDA), polyorthoester, aliphatic polyanhydride, or aromatic polyanhydride; and
b. a carrier solution.

In embodiments, the polymer, the weight average molecular weight, and the shell thickness of the semi-permanent, disappearing tattoo ink are configured such that at least one of a bioabsorption profile and a biodegradation profile exhibits a lag phase of about 2 weeks or about 4 weeks.

In embodiments:
a. the carrier solution is a liquid;
b. the particles have a diameter of less than or equal to 100 μm.

In embodiments, the semi-permanent, disappearing tattoo ink comprises:
a. particles, wherein the particles comprise:
i. a shell comprising bioabsorbable and biodegradable polymer; and
ii. a core comprising a coloring agent having a molecular weight between about 5 and about $10 \times 10^6$ Daltons; wherein said coloring agent is encapsulated by the shell polymer wherein the shell bioabsorbable and biodegradable polymer comprises a first block or diblock polymer chosen from one or a combination of: polycaprolectone (PCL), poly L-lactic acid (PLLA), poly(lactic-co-glycolic acid) (PLGA), polyethylene glycol (PEG), polyethylene glycol-diacrylate (PEGDA), polyorthoester, aliphatic polyanhydride, poly(sebacic anhydride) (poly(SA)), or aromatic polyanhydride; and (ii)
b. a carrier solution.

In embodiments, the polymer, the weight average molecular weight, and the shell thickness of the semi-permanent, disappearing tattoo ink are configured such that at least one of a bioabsorption profile and a biodegradation profile exhibits a lag phase of about 2 weeks or about 4 weeks.

In embodiments:
a. the carrier solution is a liquid;
b. the particles have a diameter of less than or equal to 100 μm.

This invention also provides a method for marking a patient for radiation therapy comprising a step of tattooing the patient with a semi-permanent, disappearing tattoo ink.

In embodiments, the method comprises tattooing the patient only once with the semi-permanent, disappearing tattoo ink and wherein the semi-permanent tattoo ink remains visible to the naked eye for between 4 weeks and 18 months after it is tattooed on the patient's skin.

In embodiments, marking the patient comprises tattooing:
a. one or more marks identifying a location of treatment,
b. one or more alignment marks,
c. one or more triangulation marks, and/or
d. one or more biangulation marks.

In embodiments, the one or more marks are tattooed with a precision of less than 1 millimeter.

In embodiments, the step of tattooing the patient with a semi-permanent, disappearing tattoo ink is performed with a sterile, single-use tattoo device comprising:
a. a hypodermic safety needle, and
b. an ampoule containing the semi-permanent, disappearing tattoo ink.

In embodiments, the semi-permanent, disappearing tattoo ink is removed from the patient's skin by the patient's immune system after it is tattooed on a patient's skin.

In embodiments, the patient's immune system does not begin removing the semi-permanent, disappearing tattoo ink for at least 2 weeks, preferably at least 4 weeks. In embodiments, the patient's immune system begins removing the semi-permanent, disappearing tattoo ink between 2 and 6 weeks after it is tattooed on a patient's skin. In embodiments, the patient's immune system begins removing the semi-permanent, disappearing tattoo ink between 2 and 4 weeks after it is tattooed on a patient's skin.

In embodiments, the semi-permanent tattoo ink comprises:
a. particles, wherein the particles comprise:
i. a shell comprising bioabsorbable and biodegradable polymer; and
ii. a core comprising bioabsorbable and biodegradable polymers or a hydrogel matrix and a coloring agent having a molecular weight between 5 and $10 \times 10^6$ Daltons, wherein said coloring agent is intercalated, non-covalently, or covalently bound with the polymer or hydrogel matrix, and wherein the bioabsorbable and biodegradable polymer comprises a homopolymer, a copolymer, a diblock or triblock copolymer chosen from one or a combination of: polycaprolectone (PCL), poly L-lactic acid (PLLA), poly(lactic-co-glycolic acid) (PLGA), polyethylene glycol (PEG), polyethylene glycol-diacrylate (PEGDA), polyorthoester, aliphatic polyanhydride, or aromatic polyanhydride; and
b. a carrier solution.

In embodiments, the polymer, the weight average molecular weight, and the shell thickness of the semi-permanent, disappearing tattoo ink are configured such that at least one of a bioabsorption profile and a biodegradation profile exhibits a lag phase of about 2 weeks or about 4 weeks.

In embodiments:
a. the carrier solution is a liquid;
b. the particles have a diameter of less than or equal to 100 μm.

In embodiments, the semi-permanent tattoo ink comprises:
a. particles, wherein the particles comprise:
i. a shell comprising bioabsorbable and biodegradable polymer; and
ii. a core comprising a coloring agent having a molecular weight between about 5 and about $10 \times 10^6$ Daltons; wherein said coloring agent is encapsulated by the shell polymer wherein the shell bioabsorbable and biodegradable polymer comprises a first block or diblock polymer chosen from one or a combination of: polycaprolectone (PCL), poly L-lactic acid (PLLA), poly(lactic-co-glycolic acid) (PLGA), polyethylene glycol (PEG), polyethylene glycol-diacrylate (PEGDA), polyorthoester, aliphatic polyanhydride, poly(sebacic anhydride) (poly(SA)), or aromatic polyanhydride; and (ii)
b. a carrier solution.

In embodiments, the polymer, the weight average molecular weight, and the shell thickness of the semi-permanent, disappearing tattoo ink are configured such that at least one of a bioabsorption profile and a biodegradation profile exhibits a lag phase of about 2 weeks or about 4 weeks.

In embodiments:
a. the carrier solution is a liquid;
b. the particles have a diameter of less than or equal to 100 μm.

Semi-Permanent Tattoo Inks

For purposes of this patent, the terms semi-permanent and removable are interchangeable. Semi-permanent tattoo inks that naturally fade or disappear over a period of time are specifically referred to herein as semi-permanent, disappearing tattoo inks. Semi-permanent, disappearing tattoo inks that may be used with the present invention may be as described in U.S. Patent Application Publication No. US 2021/0154107 A1, the entire contents of which are hereby incorporated by reference. These semi-permanent, disappearing tattoo inks are also described in PCT Pub. No. WO 2020/033903, the entirety of the contents of which are incorporated by reference.

Thus, the semi-permanent, disappearing tattoo inks of the invention may be as described in U.S. Patent Application Publication No. US 2021/0154107 A1, in the form of a composition comprising a particle and a carrier solution as described hereinbelow and in paragraphs [0040] to [0169] of U.S. Patent Application Publication No. US 2021/0154107 A1, which are hereby specifically incorporated by reference. In one embodiment, the particle that comprises a shell and a core. In one embodiment, the shell comprises a polymer that is bioabsorbable and biodegradable. Exemplary polymers include polycaprolectone (PCL), poly D-lactic acid (PDLA), poly L-lactic acid (PLLA), poly(lactic-co-glycolic acid), (PLGA), polyethylene glycol (PEG), polyethylene glycol-diacrylate (PEGDA), polyorthoester, aliphatic polyanhydride, and/or aromatic polyanhydrides, or a block copolymer thereof.

In one embodiment, the core comprises a coloring agent having a molecular weight of about 5 to about $10 \times 10^6$ Daltons.

In one embodiment, the carrier solution is a liquid, solid, semi-solid, gel, paste, or wax.

In one embodiment, the particle has a diameter of less than or equal to about 100 about 90 about 80 about 70 about 60 about 50 about 40 about 30 about 20 about 15 about 10 about 9 about 8 about 7 about 6 about about 4 about 3 about 2 about 1 or about 0.5 In one embodiment, the particle is sized to induce aggregation upon incorporation into the dermis of an animal or a human.

In one embodiment, the polymer is present in the shell at a concentration effective to induce aggregation upon incorporation into the dermis of an animal or a human. Without wishing to be bound by a particular theory, hydrophobic interactions lead to aggregation of the particles in the physiological milieu. In one embodiment, electrostatic, cross-linking via surface groups, and/or polyelectrolyte interactions give rise to particle aggregation in the dermis of an animal or human. In one embodiment, the polymer is present in the particle in an amount sufficient to prevent or inhibit phagocytosis of the coloring agent.

In one embodiment, the shell has a thickness of about 0.2 μm to 10 μm, about 0.3 μm to 9 μm, about 0.4 μm to 8 μm, about 0.5 μm to 7 μm, about 0.6 μm to 6 μm, about 0.7 μm to 5 μm, about 0.8 μm to 4 μm, about 0.9 μm to 3 μm, about 1 μm to 2 μm, inclusive.

In one embodiment, the polymer has a weight average molecular weight between 50 Da to 100 kDa, inclusive. In one embodiment, the polymer is crystalline, semi-crystalline, or amorphous. In one embodiment, the polymer is cationic, anionic, or zwitterionic at physiological pH. In one embodiment, the polymer undergoes surface or bulk erosion in aqueous solution. In one embodiment, the polymer, the weight average molecular weight, and the shell thickness are configured such that at least one of a bioabsorption profile and a biodegradation profile exhibits a lag phase of about 2 months to about 12 months. After the lag phase, the coloring agent is rapidly released into dermis, absorbed, and/or degraded.

In one embodiment, the shell further comprises a thermoresponsive polymer. In one embodiment, the thermoresponsive polymer induces particle aggregation inducer upon incorporation of the composition into the dermis of an animal or a human. In a preferred embodiment, at a temperature of about 98 degrees Fahrenheit (body temperature) or higher, the particles are aggregated, and, at temperature of less than 98 degrees Fahrenheit, the particles are in a non-aggregated form. In some embodiments, the non-aggregated form of the particles facilitates administration and dispersion of the particles in a subject. In some embodiments, administration of the composition is accomplished by intradermal injection. In one embodiment, the thermoresponsive polymer is Pluronic F-127. At concentrations of 18-50%, Pluronic F-127 forms gels above 10° C. It reliquefies when cooled to below 10° C. In some embodiments, the thermoresponsive polymer is Poly(N-isopropylacrylamide) (PNIPAM), which can be present in the shell in an range of about 0.1% to about 50%, about 0.2% to about 50%, about 0.3% to about 50%, about 0.4% to about 50, about 0.5% to about 50%, about 1% to about 50%, about 2% to about 50%, about 0.1% to about 5%, about 3% to about 50%, about 4% to about 50%, about 5% to about 50%, about 10% to about 50%, about 15% to about 50%, about 20% to about 50%, about 25% to about 50%, about 30% to about 50%, about 35% to about 50%, about 40% to about 50%, about 45% to about 50%, about 0.1% to about 49%, about 0.1% to about 48%, about 0.1% to about 47%, about 0.1% to about 46%, about 0.1% to about 45%, about 0.1% to about 40%, about 0.1% to about 35%, about 0.1% to about 30%, about 0.1% to about 25%, about 0.1% to about 20%, about 0.1% to about 15%, about 0.1% to about 10%, about 0.1% to about 5%, about 0.1% to about 4%, about 0.1% to about 3%, about 0.1% to about 2%, or about 0.1% to about 1% w/w (PNIPAM/particle weight).

In one embodiment, the coloring agent is a dye or a pigment. In one embodiment, the coloring agent is fluorescent or phosphorescent. In one embodiment, the coloring agent is present in the core in an amount between 1 ng and 1 inclusive. In some embodiments, the composition comprises a coloring agent chosen from one or a combination of the following non-limiting examples: melanin, [Phthalocyaninato(2-)] copper, FD&C Red 40 (Food Red 17, Allura Red), FD&C Yellow 5, Nigrosin, Reactive Black 5, Acid Blue 113, Brilliant black BN Granular (Food Black 1), D&C Yellow 10, FD&C Blue 1 (Food Blue 2), FD&C Blue 2, Acid Black t, Acid Black 24, Acid Black 172, Acid Black 194, Acid Black 210, *Spirulina* Extract Powder, *Gardenia* Yellow 98%, *Gardenia* Yellow 406, *Gardenia* Black, *Gardenia* Blue, *Gardenia* Red, Cochineal/Carmine, Annatto, Beta carotene. D&C Orange 4, D&C Red 33, D&C Red 22, Ext D&C Violet 2, D&C Yellow 8, FD&C Green 3, FD&C Red 4, FD&C Yellow 6, FD&C Red 3, Ponceau 4R, Acid Red 52, Carmoisine, Amamath, Brown HT, Black PN, Green S, Patent Blue V, Tartrazine, Sunset Yellow, Quinolline Yellow, Erythrosine, Brilliant Blue, Indigo Carmine, D&C Green 5, D&C Red 17, D&C Red 21, D&C Red 27, D&C Yellow 11, D&C Violet 2, D&C Green 6, D&C Red 30, D&C Red 31, D&C Red 28, D&C Red 7, D&C Red 6, D&C Red 34, D&C Yellow 10, Fake of Carmoisine, Fake of Ponceau 4R, Fanchon Yellow, Toluidine Red, Fake of Acid red 52, Fake of Allura Red, Fake of Tartrazine, Fake of Sunset Yellow, Fake of Brilliant Blue, Fake of Erythrosine, Fake of Quinoline, Fake of Indigo Carmine, Fake Patent Blue V, Fake Black PN, Fithol Rubin B, Iron Oxide Red, Iron Oxide Yellow, Iron Oxide Black, Iron Blue, Titanium Dioxide, D&C Red 36, Carbon Black, Ultramarine Blue, Ultramarine Violet, Ultramarine Red/Pink, Chromium Oxide Green, Mica, Chromium Hydroxide Green, Talc, Manganese Violet, Iron Oxide Burgundy, Iron Oxide Sienna, Iron Oxide Tan, Iron Oxide Amber, Iron Oxide Brown-G, Iron Oxide Brown S Sodium Copper Chlorophyllin, Caramel, Riboflavin, Canthaxanthin, Paprika, D&C Green 8, Ext D&C Yellow 7, NOIR Brilliant BN, Ferric Ammonium Ferrocyanide, D&C Yellow 10 Fake, FD&C Yellow 5 Fake, FD&C Yellow 6 Fake, D&C Red 21 Fake, D&C Red 33 Fake, FD&C Red 40 Fake, D&C Red 27 Fake, D&C Red 28 Fake, FD&C Blue 1 Fake, D&C Red 30 Fake, D&C Red 36 Fake, D&C Red 6 Fake, D&C Red 7 Fake, D&C Black 2. Combinations of coloring agents are contemplated by the disclosure in such concentrations that are cosmetically effective, such that release into dermis or breaks down in a lag phase in about 2 months to about 12 months. Release and degradation of the contents of each particle layer may result in a partial or full color change of the tattooed design.

In one embodiment, the core consists of the coloring agent, and the coloring agent is an aggregate. In one embodiment, the particle has a diameter of less than or equal to about 10 µm, about 9 µm, about 8 µm, about 7 µm, about 6 µm, about 5 µm, about 4 µm, about 3 µm, about 2 µm, about 1 µm, or about 0.5 µm. In one embodiment, the coloring agent is dissolved or suspended throughout the particle, which need not have a core-shell structure.

In one embodiment, the core further comprises a core polymer. In one embodiment, the polymer and the core polymer are the same or different. In one embodiment, at least one of the polymer and the core polymer is the block copolymer. In one embodiment, the block copolymer comprises a diblock copolymer or a triblock copolymer. In one embodiment, the core polymer is present in the particle at a concentration of about 7%-10%, about 10%-15%, about 15%-20%, about 20%-25%, about 25%-30%, about 30%-35%, about 35%-40%, about 40%-45%, about 45%-50%, about 50%-55%, about 55%-60%, about 60%-65%, about 65%-70%, about 70%-75%, about 75%-80%, about 80%-85%, about 85%-90%, or about 90%-92% w/w.

In one embodiment, the coloring agent is adsorbed to, physically entrapped by, or covalently bonded to the core polymer. Without wishing to be bound, it is hypothesized that, with respect to the semi-permanent, disappearing tattoo inks described in U.S. Patent Application Publication No. US 2021/0154107 A1, as the core polymer degrades, the coloring agent releases into dermis with the degraded polymer components and both are removed by the body. In one embodiment, the coloring agent comprises a metal that forms a co-ordinate bond with the core polymer. In one embodiment, the coloring agent is at a concentration of about 0.01% to 10% w/w, 0.02% to 9%, 0.03% to 8%, 0.04% to 7%, 0.05% to 6%, 0.06% to 5%, 0.07% to 4%, 0.08% to 3%, 0.09% to 2%, 0.1% to 1% inclusive, based on a total polymer weight of the particle.

In one embodiment, the core comprises the hydrogel. In one embodiment, the coloring agent is adsorbed to, physically entrapped by, intercalated, non-covalently, or covalently bound with the core polymer covalently bonded to the hydrogel. In one embodiment, the hydrogel comprises at least one of: alginate, chitosan hydrochloride, methacrylate modified hyaluronic acid (HA-MA), thiolated hyaluronic acid (HA-SH), poly(N-isopropylacrylamide) (PNIPAM), and polyethylene glycol (PEG). In one embodiment, the hydrogel comprises a salt of such hydrogels. In some embodiments, the coloring agent comprises a metal that forms a co-ordinate bond with the hydrogel.

In one embodiment, the core further comprises at least one of the following: alginate, pectin, chitosan, hyaluronic acid, x-carrageenan, agarose, agar, cellulose derivatives, carboxy methyl cellulose (CMC), protein-based hydrophilic polymers, collagen hydrolysate, gelatin, synthetic hydrophilic polymers, polyacrylamide, polyacrylic acid, polyvinyl alcohol, polyethylene glycol (PEG) and modified PEG. In one embodiment, the shell or the core further comprises at least one polyanhydrides selected from the group consisting of: poly[bis(p-carboxyphenoxy)methane)](poly(CPM)), poly[1,3-bis(p-carboxyphenoxy)propane)]poly(CPP), poly[1,6-bis(p-carboxyphenoxy)hexane](poly(CPH)), poly(sebacic anhydride) (poly(SA)), Poly[1,4-bis(hydroxyethyl)terephthalate-alt-ethyl oxyphosphate], and Poly[1,4-bis(hydroxyethyl)terephthalate-alt-ethyloxyphosphate]-co-1,4-bis(hydroxyethyl)terephthalate-co-terephthalate (P(BHET-EOP/BHET), 80/20). In one embodiment, the shell or the core further comprises at least one polyorthoester (POE) selected from the group consisting of: POE I, POE II, POE III, and POE IV, POE I, POE II, POE III, and POE IV are 1st, 2nd, 3rd and 4th generation polyorthoesters, respectively. In one embodiment, the polyorthoesters include a heterocyclic ring.

In one embodiment, the particles are present in the carrier solution at a concentration of about 5 to about 20, about 20 to about 50, about 50 to about 80, about 80 to about 110, about 110 to about 140, about 140 to about 170, about 170 to about 200, about 200 to about 230, about 230 to about 250, about 250 to about 280, about 280 to about 310, about 310 to about 340, about 340 to about 370, about or 370 to about 400 mg/mil. The concentration of particles can also be expressed as a, wherein $$\% \ w/v = \frac{\text{grams of particle}}{\text{ml composition}} \times 100\%.$$

In one embodiment, the particles are present in the carrier solution at a concentration of about 5 to about 8, about 8 to about 11, about 11 to about 14, about 14 to about 17, about 17 to about 20, about 20 to about 23, about 23 to about 25, about 25 to about 28, about 28 to about 31, about 31 to about 34, about 34 to about 37, about 37 to about 40, about 37 to about 40, about 40 to about 43, about 43 to about 45, about 45 to about 48, about 48 to about 50, about 50 to about 53, about 53 to about 55, about 55 to about 58, or about 58 to about 60% w/v. In one embodiment, the composition is at a concentration sufficient to maintain osmotic pressure within the particle for at least about 2 months to about 60 months.

In one embodiment, the composition further comprises a humectant, a biocide, a buffer, a surfactant, and/or a copolymer.

Without wishing to be bound by a specific theory, it is hypothesized that with the semi-permanent, disappearing inks described in U.S. Patent Application Publication No. US 2021/0154107 A1, following injection of the ink particles onto a region of skin, the ink particles reside in the interstitial space between dermal cells where they form large aggregates. Additionally, tattoo ink particles invoke a foreign-body inflammatory reaction that is composed of epithelioid cells, lymphocytes, and giant cells that attempt to engulf and internalize the foreign tattoo ink particles and ink particle aggregates. Macrophages and dendritic cells become enlarged and develop into epithelioid cells and multinucleated giant cells. This type of reaction, the size of the ink particle aggregates, and the collagen network surrounding the aggregates are largely responsible for maintaining tattoo ink in the dermis over longer period. As such, after administering the tattoo ink into the dermis, aggregation propensity of particles is crucial for maintaining stability of tattoos during a lag phase in which the shell is expected to bioasorb and/or biodegrade. Smaller particles have higher aggregation propensity due to their larger surface area. Therefore, an appropriate particle size range is necessary for ensuring aggregation and achieving good tattoo vibrancy over time. In some embodiments, the particle size is no more than about 100 microns in diameter.

Reduced Lag-Phase Semi-Permanent Tattoo Inks

In U.S. Patent Application Publication No. US 2021/0154107 A1, the polymer, the weight average molecular weight, and the shell thickness of the semi-permanent, disappearing tattoo inks are configured such that at least one of a bioabsorption profile and a biodegradation profile exhibits a lag phase of about 2 months to about 12 months. In one embodiment of the invention described herein, the polymer, the weight average molecular weight, and the shell thickness of the semi-permanent, disappearing tattoo inks are configured such that at least one of a bioabsorption profile and a biodegradation profile exhibits a lag phase of about 2 months to about 12 months. However, in a particularly preferred embodiment of the invention described herein, the polymer, the weight average molecular weight, and the shell thickness of the semi-permanent, disappearing tattoo ink are configured such that at least one of a bioabsorption profile and a biodegradation profile exhibits a lag phase of about 2 weeks, about 4 weeks, or about 6 weeks.

Further Embodiments

As shown in FIG. 1, semi-permanent ink is stored in an ink reservoir. The ink may be mechanically pushed down by light finger pressure squeezing or capillary action. The pen may have a sharp point, needle, or prick for the intradermal application of the semi-permanent ink.

The present invention provides for the use of semi-permanent or removable tattoo ink for the application of markings on patients for medical treatment. The semi-permanent tattoo ink of the invention remains visible for several months and naturally fades by removal of the pigment or dye by the body's immune system. The use of semi-permanent ink is advantageous for medical marking of radiation therapy patients because typical treatment plans for cancer patients receiving radiation therapy can be anywhere from a few days to a few months.

Any applicator for applying tattoo ink can be used for applying the tattoo ink of the invention. For example, the device can be any form of ink reservoir, with or without an intradermal application device, such as a needle, prick, or sharp point pen, pre-loaded with the semi-permanent or removable tattoo ink. Advantageously, the applicator can be specifically designed for use in the medical field. For example, the device may be manufactured and packaged under sterile conditions, preserving sterility until use on the patient. The ink can be semi-permanent in that it naturally fades or disappears over a period of time, or it can be removable with an outside removable agent.

Advantageously, the semi-permanent tattoo ink and devices of the present invention may be used to mark patients for radiation therapy. The semi-permanent tattoo ink and devices of the present invention may be used to mark patients for invasive or plastic surgery.

The semi-permanent tattoo ink may be pre-loaded into an ink reservoir, attached to a pen or small capillary to apply to the outer layer of skin of the patient. The pen may be equipped with a needle for application into intradermal layers of the skin. Advantageously, the device may be sealed to prevent ink leakage prior to use.

The semi-permanent tattoo ink may be pre-loaded into a micro reservoir that can range in size from a few microliters to a milliliter in volume, intended for single use. Advantageously, the micro reservoir may also be sealed to prevent ink leakage prior to use.

The semi-permanent tattoo ink may be pre-loaded into a syringe, equipped with or without a needle for intradermal application. Advantageously, the syringe may be sealed to prevent ink leakage prior to use.

The needle, prick, or sharp pointed object may be loaded into a coiled spring apparatus for the controlled and quick injection of the semi-permanent ink intradermally. The semi-permanent ink may be packaged separately or pre-loaded at the tip of the needle for immediate and convenient application.

The medical device may be packaged together with other medical equipment for the safe and sterile application of the tattoo to the patient, including but not limited to gauze, alcohol or other site preparative wipes or pads, needle, prick, or sharp pointed object for intradermal application, gloves. This package is a one-time use sterile kit for the ease of tattoo marking application by radiation therapists, technologists, nurses, or other healthcare professionals.

This invention provides a semi-permanent tattoo ink configured for use in marking a patient for medical treatment.

In embodiments, semi-permanent tattoo ink is removable ink.

In embodiments, the ink is removed by the patient's immune system.

In embodiments, the ink is removed by administration of a composition for removing the ink.

In embodiments, the ink remains visible to the naked eye for at least 4 weeks.

In embodiments, the ink remains visible to the naked eye for less than one year.

This invention also provides a device for administering the semi-permanent tattoo ink of the invention.

In embodiments, the device is a pen or a syringe.

DISCUSSION

The use of permanent tattoo ink in radiation therapy permanently "scars" patients receiving treatment with undesirable and widespread markings. Moreover, patients suffering from cancer with religious beliefs that conflict with the use of permanent tattoo ink may reject treatment. Conversely, traditional ink markers or pens, are inadequate for marking patients for radiation therapy due to their temporary nature, lasting only about 2 to 48 hours. The tattoo devices and methods described herein solve these problems by marking the patient's skin in a manner which remains visible to the naked eye for the duration of therapy while degrading and disappearing afterwards.

Further, the semi-permanent, disappearing inks described herein advantageously do not begin to fade until the completion of radiation therapy. This is accomplished by use of a semi-permanent, disappearing tattoo ink which exhibits a "lag phase" as described herein. In this preferred embodiment, the polymer, the weight average molecular weight, and the shell thickness of the semi-permanent, disappearing tattoo ink are configured such that at least one of a bioabsorption profile and a biodegradation profile exhibits a lag phase of about 2 weeks, about 4 weeks, or about 6 weeks. During this lag phase, the coloring agent is maintained in the dermis and the visibility of the tattoo ink remains relatively constant. After the lag phase, the coloring agent is rapidly released into dermis, absorbed, and/or degraded. In particularly preferred embodiments, the patient's immune system does not begin degrading the semi-permanent, disappearing tattoo ink until at least about 2 or 4 weeks, thus providing a marking that does not begin to fade until therapy has completed, but fades rapidly once therapy has completed.

General

All combinations of the various elements disclosed herein are within the scope of the invention.

The term "about" as used herein when referring to a measurable value such as an amount, a temporal duration, and the like, is meant to encompass variations of ±20%, ±10%, ±5%, ±1%, ±0.9%, ±0.8%, ±0.7%, ±0.6%, ±0.5%, ±0.4%, ±0.3%, ±0.2% or ±0.1% from the specified value, as such variations are appropriate to perform the disclosed methods.

As used herein, all headings are simply for organization and are not intended to limit the disclosure in any manner. The content of any individual section may be equally applicable to all sections. All combinations of the various elements disclosed herein are within the scope of the invention.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

What is claimed is:

1. A sterile, single-use tattoo device comprising:
   i) a hypodermic safety needle, and
   ii) an ampoule made of plastic containing a semi-permanent, disappearing tattoo ink and a breakable membrane which allows ink to flow at the time of tattoo application;
   wherein the semi-permanent, disappearing tattoo ink only remains visible to the naked eye for between 4 weeks and 18 months after it is tattooed on a patient's skin, is removed by the patient's immune system after it is tattooed on a patient's skin wherein the patient's immune system begins removing the semi-permanent, disappearing tattoo ink between 2 and 6 weeks after it is tattooed on a patient's skin, and wherein the semi-permanent, disappearing tattoo ink comprises:
   a) particles, wherein the particles comprise:
      i) a shell comprising bioabsorbable and biodegradable polymer; and
      ii) a core comprising:
         I) bioabsorbable and biodegradable polymers or a hydrogel matrix and a coloring agent having a molecular weight between 5 and $10 \times 10^6$ Daltons, wherein said coloring agent is intercalated, non-covalently, or covalently bound with the polymer or hydrogel matrix, and wherein the bioabsorbable and biodegradable polymer comprises a homopolymer, a copolymer, a diblock or triblock copolymer chosen from one or a combination of: polycaprolectone (PCL), poly L-lactic acid (PLLA), poly(lactic-co-glycolic acid) (PLGA), polyethylene glycol (PEG), polyethylene glycol-diacrylate (PEGDA), polyorthoester, aliphatic polyanhydride, or aromatic polyanhydride; or
      II) a coloring agent having a molecular weight between about 5 and about $10 \times 10^6$ Daltons; wherein said coloring agent is encapsulated by the shell polymer wherein the shell bioabsorbable and biodegradable polymer comprises a first block or diblock polymer chosen from one or a combination of: polycaprolectone (PCL), poly L-lactic acid (PLLA), poly(lactic-co-glycolic acid) (PLGA), polyethylene glycol (PEG), polyethylene glycol-diacrylate (PEGDA), polyorthoester, aliphatic polyanhydride, poly(sebacic anhydride) (poly(SA)), or aromatic polyanhydride; and
   b) a carrier solution.

2. The sterile, single-use tattoo device of claim 1, wherein the semi-permanent, disappearing tattoo ink remains visible to the naked eye for less than one year after it is tattooed on a patient's skin.

3. The sterile, single-use tattoo device of claim 1, wherein:
   i) the carrier solution is a liquid;
   ii) the particles have a diameter of less than or equal to 100 μm.

4. A method for marking a patient for radiation therapy comprising a step of tattooing the patient with a semi-permanent, disappearing tattoo ink, wherein:
   i) the method comprises tattooing the patient only once with the semi-permanent, disappearing tattoo ink, and the semi-permanent, disappearing tattoo ink is removed from the patient's skin by the patient's immune system after it is tattooed on the patient's skin, wherein the patient's immune system removing the semi-permanent, disappearing tattoo ink between 2 and 6 weeks after it is tattooed on the patient's skin;
   ii) the semi-permanent tattoo ink remains visible to the naked eye for between 4 weeks and 18 months after it is tattooed on the patient's skin;
   iii) the semi-permanent tattoo ink comprises:
   a) particles, wherein the particles comprise:
      I) a shell comprising bioabsorbable and biodegradable polymer; and
      II) a core comprising:
         a) bioabsorbable and biodegradable polymers or a hydrogel matrix and a coloring agent having a molecular weight between 5 and $10 \times 10^6$ Daltons, wherein said coloring agent is intercalated, non-covalently, or covalently bound with the polymer or hydrogel matrix, and wherein the bioabsorbable and biodegradable polymer comprises a homopolymer, a copolymer, a diblock or triblock copolymer chosen from one or a combination of: polycaprolectone (PCL), poly L-lactic acid (PLLA), poly(lactic-co-glycolic acid) (PLGA), polyethylene glycol (PEG), polyethylene glycol-diacrylate (PEGDA), polyorthoester, aliphatic polyanhydride, or aromatic polyanhydride; or
         b) comprising a coloring agent having a molecular weight between about 5 and about $10 \times 10^6$ Daltons; wherein said coloring agent is encapsulated by the shell polymer wherein the shell bioabsorbable and biodegradable polymer comprises a first block or diblock polymer chosen from one or a combination of: polycaprolectone (PCL), poly L-lactic acid (PLLA), poly(lactic-co-glycolic acid) (PLGA), polyethylene glycol (PEG), polyethylene glycol-diacrylate (PEGDA), polyorthoester, aliphatic polyanhydride, poly(sebacic anhydride) (poly(SA)), or aromatic polyanhydride; and b) a carrier solution.

5. The method of claim 4, wherein marking the patient comprises tattooing:
 i) one or more marks identifying a location of treatment,
 ii) one or more alignment marks,
 iii) one or more triangulation marks, or
 iv) one or more biangulation marks.

6. The method of claim 4, wherein the one or more marks are tattooed with a precision of less than 1 millimeter.

7. The method of claim 4, wherein the step of tattooing the patient with a semi-permanent, disappearing tattoo ink is performed with a sterile, single-use tattoo device comprising:
 i) a hypodermic safety needle, and
 ii) an ampoule containing the semi-permanent, disappearing tattoo ink.

8. The method of claim 4, wherein:
 i) the carrier solution is a liquid;
 the particles have a diameter of less than or equal to 100 µm.

* * * * *